United States Patent [19]

United States Patent [19]

Abrams et al.

[11] Patent Number: 5,043,270
[45] Date of Patent: Aug. 27, 1991

[54] INTRONIC OVEREXPRESSION VECTORS

[75] Inventors: John M. Abrams, New York, N.Y.; Robert T. Schimke, Palo Alto, Calif.; Susan M. Thorpe, Copenhagen, Denmark

[73] Assignee: The Board of Trustees of the Leland Stanford Junior University, Stanford, Calif.

[21] Appl. No.: 331,434

[22] Filed: Mar. 31, 1989

[51] Int. Cl.$^5$ .................... C12N 1/00; C12N 15/12; C12N 15/11; C12N 5/00
[52] U.S. Cl. .................... 435/69.1; 435/172.3; 435/240.1; 435/320.1; 536/27; 935/34; 935/61; 935/66; 935/70; 935/71; 935/79; 935/84
[58] Field of Search ............ 435/69.1, 70.1, 70.3, 435/172.1, 172.3, 240.1, 240.2, 320, 320.1; 536/27; 935/22, 29, 34, 42, 61, 66, 70, 71, 79, 84

[56] References Cited

PUBLICATIONS

"Expression of Abbreviated Mouse Dihydrofolate Reductase Genes in Cultured Hamster Cells" Gasser et al., (1982) *Proc. Natl. Acad. Sci. USA*, 79: 6522–6526.

"Molecular Cloning of the neu Gene: Absence of Gross Structural Alteration in Oncogenic Alleles" Hung et al., (1986) *Proc. Natl. Acad. Sci. USA*, 83: 261–264.

"Gene Within a Gene: Nested Drosophila Genes Encode Unrelated Proteins on Opposite DNA Strands" Henikoff et al., (1986) *Cell*, 44: 33–42.

"Methotrexate-Induced Amplification of the Bovine Lutropin Genes in Chinese Hamster Ovary Cells" Kaetzel et al., (1988) *Journal of Biological Chemistry*, 263: 6344–6351.

"Coamplification and Coexpression of Human Tissue-Type Plasminogen Activator and Murine Dihydrofolate Reductase Sequences in Chinese Hamster Ovary Cells" Kaufman et al. (1985) *Molecular and Cellular Biology*, 5: 1750–1759.

"Competitive Inhibition of hsp70 Gene Expression Causes Thermosensitivity" Johnston et al., (1988) *Science*, 242: 1551–1554.

"Amplification and Expression of Sequences Cotransfected with a Modular Dihydrofolate Reductase Complementary DNA Gene" Kaufman et al., (1982) *Journal of Molecular Biology*, 159: 601–621.

*Primary Examiner*—James Martinell
*Attorney, Agent, or Firm*—Bertram I. Rowland

[57] ABSTRACT

DNA constructs are provided employing intronically positioned expression, systems, where one of the genes is a dominant gene, usually amplifiable, and the other gene encodes a sequence of interest. Higher levels of co-expression are achieved than when the genese are ligated in tandem. Specifically, the gene of interest is inserted into the intron of a DHFR minigene, the construct transformed into a mammalian cell and the resulting transformants stressed with progressively increasing levels of methotrexate. Substantially increasing levels of co-expression are achieved with increasing levels of methotrexate.

26 Claims, No Drawings

5,043,270

INTRONIC OVEREXPRESSION VECTORS

This invention was supported in part under a grant from the NIH (NIH Grant No. GM 14931), an NCI Foreign Exchange fellowship, and The Danish Cancer Society.

INTRODUCTION

TECHNICAL FIELD

The subject field concerns amplification and expression of recombinant genes

BACKGROUND

Biological research and applications in biotechnology often require cell lines that express high levels of a given gene product. As an increasing number of genes are isolated and developed for the production of a wide array of useful polypeptide drugs, there is an increasing need to enhance the efficiencies and economies of manufacture. Much of the effort in this direction has been directed to the use of strong promoters, enhancers, high copy number plasmids, and amplification using an amplifiable gene.

While amplification appears to be an attractive approach, nevertheless it has many limitations. The amplification process has normally involved ligating in tandem the amplifiable gene and the gene of interest, where each of the genes has an independent transcriptional initiation region. For the most part, this approach while showing some promise has not proven to be as useful a might have been hoped. The level of amplification has been limited. In addition, the tandem sequences have been unstable in that in the absence of continuous selective pressure, copies of the gene may be looped out and lost. Since selective pressure normally reduces the viability of the cells, there is an interest in being able to develop systems to provide for stable enhancement of expression of a desired gene.

RELEVANT LITERATURE

Reference directed to co-transfection of a gene together with a genetic marker which allows for selection and subsequent amplification include: Kaufman in *Genetic Engineering*, ed. J. Setlow (Plenum Press, New York) Vol. 9 (1987); Kaufman and Sharp, *J. Mol. Biol.* 159:601 (1982); Ringold, et al., *J. Mol. Appl. Genet.* 1:165–175 (1981); Kaufman, et al., *Mol. Cell Biol.* 5:1750–1759 (1985); Kaetzel and Nilson, *J. Biol. Chem.* 263: 6244–6751 (1988); Hung, et al., *Proc. Nat'l. Acad. Sci., USA* 83:261–264 (1986); Kaufman, et al., *EMBO J.* 6:87–193 (1987); Johnston and Kucey, *Science* 242:1551–1554 (1988); Urlaub, et al., *Cell* 33:405–412 (1983) and Urlaub and Chasin, *Proc. Natl. Acad. Sci. USA* 77:4215–4220 (1980). Use of mutant forms of a DHFR gene having reduced affinities for MTX are reported by Wigler, et al., *Proc. Natl. Acad. Sci. USA* 77:3567–3570 (1980); Haber and Schimke *Somatic Cell Genetics* 8:499–508. MTX resistance in DHFR transformants is at least partially conferred by varying degrees of gene amplification. Schimke, *Cell* 37:705–713 (1984). The inadequacies of co-expression of the non-selected gene have been reported by Wold, et al., *Proc. Natl. Acad. Sci. USA* 76:5684–5688 (1979). Instability of the amplified DNA is reported by Kaufman and Schimke *Mol. Cell Biol.* 1:1069–1076 (1981), Haber and Schimke *Cell* 26:355–362 and Fedespiel, et al., *J. Biol. Chem.* 259:9127–9140 (1984). The existence of an independently regulated intronic protein coating gene has a biological precedent in Drosophila as reported by Henikor, et al., *Cell* 44:33–42 (1986).

SUMMARY OF THE INVENTION

Novel DNA constructs are provided comprising a gene having at least one intron and a second gene inserted into said at least one intron. Each of the genes have their own transcriptional and translational regulatory regions, so as to be independently expressible, wherein one of the genes is desirably an amplifiable gene. The constructs are introduced into eukaryotic hosts for integration into the eukaryotic genome, followed by selection for the selectable gene, using increasing concentrations of the selection agent for amplification. The resulting products are found to have high levels of expression of the non-selectable gene as a result of co-amplification of the two genes.

DESCRIPTION OF THE SPECIFIC EMBODIMENTS

Methods and compositions are provided for enhancing the stability and/or copy number of a transcribed sequence in order to allow for elevated levels in the nucleus of an RNA sequence of interest. The DNA constructs comprise two genetic elements, an external gene comprising at least one intron having its own transcriptional and translational initiation and termination regulatory regions, and an internal genetic element comprising a gene within the intron, usually having independent transcriptional and translational initiation and termination regulatory regions. Thus, the construct will comprise a dominant, usually an amplifiable gene, which comprises an intron in which a sequence of interest is inserted or a gene of interest comprising an intron in which the dominant gene is inserted, usually the former.

A wide variety of dominant genes of interest other than amplifiable genes exist, such as Neomycin resistance from Tn5, Hygromycin resistance from *E. coli*, GPT gene from *E. coli*, and the like. Amplifiable genes include dihydrofolate reductase, amplifiable with methotrexate or methotrexate analogs, metallothioneins, I & II, amplifiable with heavy metals, such as mercury, lead, cadmium copper, etc., adenosine deaminase, which is amplifiable with adenine, azaserine or coformycin, CAD amplifiable by PALA, UMP-synthetase amplifiable by 6-azauridine, Xyl-A, or adenosine alanosine and 2'-deoxycoformycin, IMP-5'-dehydrogenase and *E. coli* XGPT amplifiable with mycophenolic acid, glutamine synthetase amplifiable with methionine sulfoximine, HMG CoA reductase amplifiable with compactin, thymidylate synthetase amplifiable with 5-fluorodeoxyuridine, ribonucleotide reductase amplifiable with aphidicolin, N-acetyl-glucosaminyl transferase amplifiable with tunicamycin, $Na^+$-$K^+$ ATPase amplifiable with ouabain, or the like. See also, Kaufman, R. J. (1987) in *Genetic Engineering* 9 (J. Setlow ed.), Plenum Press, N.Y., p. 171. While the above genes have found extensive use as amplifiable genes, as other amplifiable genes become available, these too may be used in accordance with the subject invention.

For purposes of discussion, the gene within the intron will be referred to a the internal gene, and the gene comprising the intron will be referred to as the external gene. The external gene will always have at least one intron and may have two or more, usually having fewer than the natural gene, generally having not more than about 30% of the nucleotides from the 5'- terminus to the 3'-terminus as introns. The internal gene will usually be free of introns, but may have one or more introns depending upon the particular nature of the gene. The introns may be within the coding region, that is between exons, or external to the coding region, that is in the 5'- or 3'-untranslated regions, where the introns will be excised during processing of the messenger. The intron may be modified by introduction of a polylinker for ease of insertion of a sequence of interest.

For the most part, the internal gene will be a gene encoding a protein of interest. There may be one or more internal genes within the same or different introns, usually not more than about 3. The internal gene will include independent transcriptional and translational regulatory regions, to allow for expression of the internal gene. However, in some instances it may be desirable to produce an anti-sense sequence where one wishes to inhibit the expression of the gene present in the host. In this situation, one may or may not wish to have an independent transcriptional initiation regulatory region or transcriptional termination regulatory region for the anti-sense sequence. However, one will usually desire to have independent initiation of the antisense sequence, to allow for a higher level of the anti-sense sequence in the nucleus. The anti-sense sequence will usually be at least about twelve nucleotides, more usually at least about fifteen nucleotides and, may be 2 knt or more. The anti-sense sequence will be complementary to an mRNA of a host gene which is expressed.

The gene of interest may be any sequence which encodes a protein of interest or encodes a sequence which inhibits the expression of a protein of interest. A wide variety of mammalian proteins have been produced and the number keeps increasing. These proteins include blood proteins, such as serum albumin, erythropoietin, colony stimulating factors, such as granulocyte and monocyte CSFs, interleukins, interferons, plasminogen activator, FVIIIc, as well as other blood factors, monokines, cytokines, etc.; structural proteins, such as actin, myosin, tubulin, collagen, keratin, etc.; industrial enzymes such as chymosin, lipases, proteases, etc.; other proteins, such as globin, surface membrane receptors, major histocompatibility, complex antigens, etc. Of course, the list could be greatly extended. In addition, anti-sense sequences may be of interest in inhibiting the expression of various genes, such as betagalacturonase, globin, oncogenes, "anti-oncogenes," hormone receptor genes, G-proteins, protein kinases, etc.

The transcriptional initiation in the regulatory regions may be constitutive or inducible. Thus, one can provide for amplification of the amplifiable gene and then by maintaining the culture under non-permissive conditions, substantially terminate the expression of the amplifiable selectable gene. In this manner, one would avoid having high levels of expression of the amplifiable gene, during transcription and translation, as appropriate, of the gene of interest. Similarly, depending upon the nature of the gene of interest one may employ a constitutive or inducible transcriptional initiation regulatory region for expression of the gene of interest. The transcriptional initiation regions may be derived from any convenient source, and may be inducible as a result of a temperature change, the addition of an inducer, or the like. Inducible promoters include HMG CoA reductase, maltase, metallothionein, steroid hormone, etc. The transcriptional initiation region may be derived from viruses or the genome of the host or other species where the initiation region is functional in the transformant. In some instances, the transcriptional initiation regulatory region may be modified to vary the efficiency, inducibility, or the like of the initiation regulatory region. In other instances, enhancers may be employed to further increase the transcriptional efficiency. Enhancers may be obtained from the immunoglobulin, heat shock, glucocorticoid, etc. genes.

The direction of transcription of the internal and external genes may be the same or different, preferably the same. It is noted that when the external gene is an amplifiable gene and the internal gene is the gene of interest, one obtains a lower level of expression efficiency of the gene of interest where the direction of transcription is opposite.

The hosts for the subject invention will be eukaryotic cellular hosts, particularly vertebrate cellular or plant cellular hosts, which are capable of intron processing. While yeast, fungi and plants are known to be capable of processing introns, for the most part, it will be desirable to use mammalian cells. A wide variety of mammalian cells are known and can be used in culture, where the particular choice is not critical to this invention. Hosts include Chinese hamster ovary cells, mouse kidney cells, silk worm cells, yeast, i.e., any host capable of correct RNA splicing. Depending upon the product, the choice may depend upon one or another cell line. The cells may be in culture, tissue culture or part of a viable intact organ or organism. The host may also include pronuclei of fertilized eggs or embryonic stem cells for the purpose of producing transgenic animals. Also, plant protoplasts may be transfected. The host may have a positive or negative background for the amplifiable gene, preferably negative.

The gene of interest may be a secretable gene or be made so by employing a signal sequence. Thus, the gene of interest may be modified by linking the gene of interest to a signal sequence and a processing signal which allows for transport of the gene of interest into the culture medium. A large number of signal sequences have been developed for a wide variety of cellular hosts, so the particular choice of signal sequence will depend upon its efficiency in the given system, and an ample variety are available from the literature. Signal sequences which have found use include the chymosin signal sequence, immunoglobulin signal sequence, surface membrane protein receptor signal sequences, or the like. In some instances it may be of interest that the protein be integrated into a membrane, where a signal sequence (including transit peptide) and transmembrane integrator sequence will be employed.

The subject constructs may or may not be made as part of a vector. For convenience, usually in the preparation of the constructs, they will be maintained in a vector capable of replication in a prokaryotic host. The vector will normally also include a marker for selection in the prokaryotic host. A marker is normally a toxin resistant gene, particularly an antibiotic, but may also provide for complementation to an auxotrophic host. Once the construct is prepared, it may then be excised and used by itself or the entire plasmid may be transformed into the host. Conveniently, for enhanced efficiency of integration, plasmids may also include a replication system functional in the host, where the replication system for mammalian hosts may be a virus, such as Simian virus, adenovirus, papillovirus etc.; for insects, baculovirus; or the like. With plants, for the most part there will be direct integration, where various techniques may be employed for introduction of the construct into the plant.

Introduction of the subject constructs may be as a result of transfection, calcium phosphate precipitated DNA, protoplast fusion, lipofection ballistic particles, Ti plasmid transformation with plants, electroporation or the like.

The resultant transformed culture may then be selected where cells containing the subject constructs are identified by stressing the cells with the selective agent, which acts against the product of the amplifiable gene. In the case of the use of a gene expressing a product having the same function as an endogenous gene, desirably, the amplifiable gene will be at least as susceptible to the selective agent as the wild-type gene, preferably more sensitive. Also, as already indicated, it will frequently be desirable to employ a negative background for the amplifiable gene, so that it is the construct which must respond to the selective agent and not both the construct and the wild type gene.

Amplification can be achieved by slowly increasing the level of the selective agent as an amplifying agent in successive or sequential culture media, with addition of increasing amounts of the selective agent to the same or different culture media, optionally isolating and expanding the surviving cells or clones, and then subjecting these cells to further stress with the selective agent e.g., methotrexate with DHFR. The process may be repeated as many times as necessary to achieve the desired level of expression of the gene of interest which will be limited by the ability of the cell to produce the transcriptional and translational products in addition to its normal metabolism, as well as the stability of the amplified construct. Increasing copies of the construct in tandem may be achieved.

The following examples are offered by way of illustration and not by way of limitation.

EXPERIMENTAL

Fragments from pRed CAT (Osborne, et al., *Cell* 42:203-212 (1985), a hybrid HMG CoA reductase promotorchloramphenicol acetyl transferase (CAT) gene were ligated to a modular DHFR gene (pMg3) which contains the first two introns of the murine DHFR gene (Gasser, et al., supra) as well as the 5'-DHFR promoter region and about approximately 1 kb of 3'-untranslated sequence. The CAT sequences are inserted into the second intron of the DHFR minigene 3 in an orientation which either parallels (pMg3(+)HCAT) or opposes (pMg3(−)HCAT) DHFR transcription. For these constructions, as well as the controls, reporter gene (CAT) is positioned immediately 3' of a promoter that is sensitive to extracellular sterol levels (Osborne, et al., supra). To control the effects of preligation, an additional plasmid was constructed which links the reporter and marker genes in a divergent, non-overlapping fashion (pMg3(X)HCAT).

To construct the intronic expression plasmids, pMg3 [Gasser, et al., *Proc. Natl. Acad. Sci. USA* 79:6522-6526 (1982)] was partially digested with PstI and singly cleaved molecules were isolated on a Seaplaque agarose gel, #A ~4 kb product liberated by PstI digestion of pRed CAT was ligated to the partial PstI preparation of pMg3 and the resulting ligation mixture was used for bacterial transformations. Tetracyline resistant colonies were screened for appropriate inserts and diagnostic HindIII and EcoRI restriction digests allowed for the determination of insert orientation. pMg3(+)HCAT harbors the intronic CAT gene with a polarity paralleling DHFR whereas pMg3(−)HCAT carries the intronic reporter gene in the inverted orientation.

To construct the control plasmid pRed CAT was partially digested with BamHI; singly cleaved products were gel purified and ligated to a complete BamHI restriction of pMg3. The resulting plasmid, pMg3(X)HCAT, links the DHFR marker and the CAT reporter gene in a non-overlapping divergent fashion with their respective start codons separated by approximately 4.5 kb.

The vectors were transfected by calcium phosphate precipitation (Gasser, et al., supra) into a Chinese Hamster Ovary cell line which is deleted for both endogenous DHFR genes (Urlaub, et al.), *Cell* 33:45-412 (1983). As an additional control, the unlinked parental plasmids pRed CAT and pMg3 were cotransfected to simulate the most commonly used approach for over expressing heterologous proteins. To follow the behavior of these constructions during amplification, pools of transformants were stepwise selected, as described by Kaufman and Schimke, *Mol. Cell. Biol.* 1:1069-1076 (1981), in progressively higher concentrations of MTX (methotrexate). Approximately half-confluent cell monolayers were rinsed and harvested in ice-cold PBS by scraping. After centrifugation, cell pellets were washed twice with PBS, resuspended in 100 μl 0.25M Tris (pH7.6) and lysed by three cycles of freeze-thawing (−70° to 37° C.). The lysates were then heated to 60° C. for 7 min., centrifuged in a microfuge at full speed for 10 min. and the clear supernatants were frozen at −70° C. Repeated determinations showed that the freeze/thawing cycles of the concentrated cell extracts did not influence CAT activity. Protein quantitations were determined by the Bio-Rad assay. Median protein concentration of the extracts was 330 μg/ml (range:60-910 μg/ml) using BSA as a standard. Because of the unusually high levels of CAT activity present in the transfected cells, it was necessary to dilute the cell extracts in 0.25% BSA to between 5 ng/ml and 10 μg/ml before the assay. The inclusion of carrier protein was shown to be essential for accuracy and reproducibility. For CAT activity determinations, 40 μl aliquots of diluted extract were incubated with 60 μl Tris buffer containing 0.6 mM acetyl CoA and 0.15 mCi $^{14}$C-chloramphenicol (60 mMCi/mM). After a 3 hour incubation, the organic material was extracted with ethyl acetate, evaporated to dryness, resuspended in 15 μl ethyl acetate and spotted onto silica gel sheets for thin layer chromatography in CHCl$_3$:methanol (95:5). The acetylated $^{14}$C products were removed and counted for precise determinations. Assays were considered valid when only mono- but not the diacetylated product was present. Control experiments confirmed a linear relation between enzyme levels and the formation of monoacetylated product up to approximately 75% conversion of substrate.

Successively higher concentrations of methotrexate (10 nM, 20 nM, 60 nM, 200 nM, 500 nM, and 2 μM MTX were employed). The following table indicates the results.

TABLE 1

| | Methotrexate Concentration | | | | | | | | | | | |
|---|---|---|---|---|---|---|---|---|---|---|---|---|
| | 0 nM | | | 10 nM | | | 60 nM | | | 2000 nM | | |
| Vector(s) | CAT* activity | DHFR genes | CAT/DHFR ratio | CAT* activity | DHFR genes | CAT/DHFR ratio | CAT* activity | DHFR genes | CAT/DHFR ratio | CAT* activity | DHFR genes | CAT/DHFR ratio |
| Mg3(+) HCAT | 0.40 | 0.7 | 0.6 | 1.5 | 6 | 0.3 | 28.2 | 140 | 0.2 | 87.3 | 780 | 0.1 |
| Mg3(−) HCAT | 0.20 | 0.3 | 0.7 | 23.6 | 150 | 0.2 | 31.0 | 600 | 0.05 | 70.0 | 4200 | 0.02 |
| Mg3(X) HCAT | 0.02 | 0.5 | 0.04 | 1.1 | 9 | 0.1 | 10.5 | 70 | 0.15 | 48.5 | 660 | 0.07 |
| Mg3 & HCAT | 0.03 | 0.6 | 0.05 | 0.6 | 25 | 0.02 | 5.0 | 300 | 0.02 | 2.9 | 700 | 0.004 |
| Mg4Ea & HCAT | 0.01 | ND | — | 0.7 | ND | — | 1.1 | ND | — | 31.8 | ND | — |

*Units of CAT activity are expressed as % of substrate converted per ng of protein. Values for CAT activity at 0 nM, 10 nM and 60 nM represent the average of two determinations. Median coefficient of variation is 9.5% (range 0%–30%).

DHFR gene copy number is determined by densitometric comparisons with known standards. DHFR gene copy numbers at 200 nM MTX were quantitated by reference only to predicted fragment sizes even though significant hybridization signal is detected from rearranged genes.

Mg4Ea is a similar DHFR minigene construction (Gasser et al., PNAS 79:6522) which includes a ~130 bp fragment carring SV40 enhancer sequences.

In each case, determinations of CAT activity and genomic DNA was made. Among the primary transformants, it is readily apparent that intronic positioning of the reporter gene confers significantly enhanced levels of activity regardless of orientation. The greatest increase (approximately 20 fold) relative to control transformants is apparently achieved by an orientation which parallels that of DHFR expression. This enhancement extends to comparisons with cells cotransfected with pRed CAT and a similar DHFR minigene (pMg4Ea) that also carries an SV40 enhancer fragment (Gasser, et al., supra.). Reproducibility of these results was confirmed by a second round of transfections in which the transformants harboring the intronically positioned genes gave a 15–16 fold higher CAT expression relative to control pMg3(X)HCAT transformants. From the above data it is also apparent that a preligation of the templates prior to transfection offers no enhancement of reporter gene expression among the primary transformants.

To determine the true co-expression efficiency as these transformed populations are selected for DHFR amplification, reporter gene activity was normalized to DHFR gene copy number for each level of MTX resistance. As these populations are selected for increased resistance to MTX, the advantage of intronic positioning gradually dissipates during the early levels of MTX selection. Although genetic preligation does not affect the efficiency of co-expression among primary transformants, the levels of reporter activity observed during amplification are dramatically influenced by whether or not the marker gene and the reporter gene were covalently linked prior to transfection. This observation may reflect the graded nature of amplified DNA which can differentially disassociate the selected marker from the non-selected gene depending on the tightness of their original linkage. It should also be noted that the number of DHFR genes present in Mg3(−)HCAT transformants is consistently and inordinately high relative to Mg3(+) HCAT cells or control transformants at every level of antifolate selection. These results suggest that intronic opposite-strand transcription made either by steric hindrance or anti-sense mechanisms impede DHFR expression such that greater gene dosages are required for comparable levels of MTX resistance.

Sterol-mediated suppression in the presence of sterols was investigated, in view of the sterol-responsiveness of the HMG CoA reductase promoter. Although sterol-mediated regulation (three-fold) is observed from Mg3(−)HCAT primary transformants, this behavior is lost as the cells are amplified to 10 nM MTX. Mg3(+)HCAT transformants, however, display the converse behavior; i.e., regulation (three-fold) is observed under slightly amplified (10 nM MTX) circumstances but not at the primary transformant level. Once amplified to far steeper levels (200 nM MTX), neither of the intronically positioned templates show evidence of a capacity to respond to extracellular sterols.

Total RNA from transformed populations carried in 2 μM MTX for 3 to 4 weeks was analyzed. In contrast to the relatively uniform levels of DHFR RNAs present in these amplified transformants, the amount of hybridizble CAT RNA generally parallels the observed levels of CAT activity, ranging from levels which are undetectable (Mg3 and HCAT) to levels which are quite abundant Mg3(+)HCAT and Mg3(−)HCAT. Relative to amplified transformants harboring a preligated form of these two genes Mg3(x)HCAT, the levels of heterologous expression generated from the intronically positioned templates constitute even a far greater proportion of total RNA than might be inferred from the CAT activity data. DHFR specific products with sizes similar to the mRNAs generated from the endogenous murine DHFR gene (ranging from 800–1600 bp) hybridize at roughly comparable levels in all cell lines with one exception. The RNAs clustered at approximately 2 kb which are detected by the CAT probe coincide with the sizes expected of transcripts which initiate within the HMG CoA reductase promoter and polyadenylate at the SV40 signal derived from pRed CAT. Another prominent approximately 4 kb signal specifically detected in Mg3(+)HCAT transformants may represent transcripts which initiate at the intronic HMG CoA reductase promoter and terminate at the polyadenylation signals within the DHFR minigene (a similar sized RNA is detected by both DHFR and CAT probes). The other large transcripts detected by the DHFR and CAT probes do not correspond to the sizes predicted for unspliced messengers nor do they correspond to any predicted combination of known start sites and polyadenylation signals within the constructions.

Taken together, these studies demonstrate that the expression and co-amplification of foreign gene products is markedly improved by fusing a non-selectable template to the intron of an amplifiable marker minigene. Among primary transformants, the results show that intronic positioning enhances heterologous expression of the non-selected gene by 15-20 fold relative to previous approaches. Because this result is not attributable to gene dosage effects, the improvement must arise at least in part from an increased proportion of transformed clones which co-express the non-selected gene. Typical estimates of functional co-expression from independently transfected plasmids range from 15-30% and thus even the maximal improvement offered by this explanation can only partially account for the approximately 20 fold enchancement that is observed. In addition to an increased proportion of co-expressing transformants, the intronically positioned genes, on average, generate significantly higher levels of product relative to control templates.

The above data demonstrate the many advantages of intronically positioned expression systems with amplifiable genes. The advantages may be extended to other genetic systems which employ dominant marker genes and/or amplifiable marker genes (Kaufman, et al., *Proc. Natl. Aca. Sci. USA* 83:3136-3140 (1986). The system may be exploited for studies that require the screening of massive numbers of stable transformants for a particular attribute, e.g., libraries of stable transfectants. The subject amplification strategy virtually requires that the integrity of the co-amplified gene is maintained. Intronically positioned templates may also be used to explore mutation and repair phenomena under circumstances that are well defined and clearly delimit the boundaries within which these processes may occur. In addition, anti-sense sequences may be produced for regulation of endogenous unlinked genes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A non-naturally occurring DNA construct, said DNA construct comprising an external genetic element and an internal genetic element, said external genetic element comprising a primary gene, primary transcriptional initiation and termination sites, and primary transcriptional regulatory region regulating transcription of said primary gene, said primary gene containing at least one intron, said internal genetic element comprising a secondary gene, secondary transcriptional initiation and termination sites, and secondary transcriptional regulatory region regulating transcription of said secondary gene, said internal genetic element being within said at least one intron, with at least one member of the group composed of said primary gene and said secondary gene being a gene capable of selection.

2. A DNA construct of claim 1, wherein said primary gene is said gene capable of selection.

3. A DNA construct of claim 1, wherein said gene capable of selection is an amplifiable gene capable of amplification by means of a selective agent.

4. A DNA construct according to claim 3, wherein said amplifiable gene is DHFR.

5. A vector comprising a DNA construct according to claim 4.

6. A vector according to claim 5, wherein said vector is capable of replication in a prokaryotic host.

7. A vector according to claim 5, wherein said vector is capable of replication in a eukaryotic host.

8. A DNA construct of claim 1, wherein said intron is bounded by coding regions of said gene capable of selection.

9. A DNA construct of according to claim 1, wherein said secondary gene is an open reading frame capable of selection.

10. A DNA construct according to claim 1, wherein said secondary gene is an anti-sense sequence of a gene in a cellular host in which said primary and secondary transcriptional regulatory regions are functional.

11. A vector comprising a DNA construct according to claim 1.

12. A vector according to claim 11, wherein said vector is capable of replication in a prokaryotic host.

13. A vector according to claim 11, wherein said vector is capable of replication in a eukaryotic host.

14. Eukaryotic host cells in culture according to claim 1, wherein said secondary gene is an open reading frame capable of expression.

15. A method for producing a protein of interest, employing eukaryotic cells containing multiple copies of a DNA construct according to claim 1, wherein one member of said group is an amplifiable gene capable of amplification by means of a selective agent, and the other member of said group is a gene encoding the protein of interest, said method comprising:

growing said cells in a nutrient medium, whereby said protein is expressed; and harvesting said protein.

16. A method according to claim 15, wherein said nutrient medium is selective for said amplifiable gene.

17. Eukaryotic host cells in culture, said cells comprising a DNA construct according to claim 1, said DNA construct being integrated into a chromosome of said host cells.

18. Eukaryotic host cells in culture according to claim 17, wherein said primary gene is said gene capable of selection.

19. Eukaryotic host cells in culture according to claim 17, wherein said gene capable of selection is an amplifiable gene capable of amplification by means of a selective agent.

20. Eukaryotic host cells in culture according to claim 19, wherein said amplifiable gene is DHFR.

21. Eukaryotic host cells in culture according to claim 17, wherein said intron is bounded by coding regions of said gene capable of selection.

22. Eukaryotic host cells in culture according to claim 17, wherein said secondary gene is an anti-sense sequence of a gene in a cellular host in which said primary and secondary transcriptional regulatory regions are functional.

23. Eukaryotic host cells in culture according to claim 17, wherein said external and internal genetic elements are present in multiple tandem copies.

24. Eukaryotic host cells in culture according to claim 17, wherein said external and internal genetic elements are present in multiple tandem copies.

25. A method for producing eukaryotic cells having multiple copies of a sequence of interest, wherein said cell comprises introducing into said cells a DNA construct comprising two genetic elements, a first external genetic element comprising first transcriptional initiation and termination regulatory regions for transcription and a first gene comprising an intron under the transcriptional regulation of said first regulatory regions; and a second internal genetic element within said intron comprising second transcriptional initiation and termination regulatory regions and a second gene under the transcriptional regulation of said second regulatory regions, with the proviso that one of said genetic elements is a gene capable of amplification, said method comprising:

growing said cells in a selective medium comprising an amplifying agent for sufficient time for amplification to occur; and selecting cells having multiple copies of said sequence of interest.

26. A method according to claim 25, wherein said amplifying agent is sequentially raised in concentration.

* * * * *